United States Patent [19]

Yoshimura et al.

[11] 4,316,018

[45] Feb. 16, 1982

[54] CRYSTALLIZED CEPHALOSPORIN SALTS

[75] Inventors: Yoshinobu Yoshimura, Suita; Nobuhide Morikawa, Toyonaka; Kunio Takanohashi, Kawanishi, all of Japan

[73] Assignee: Takeda Chemical Industries, Ltd., Osaka, Japan

[21] Appl. No.: 147,053

[22] Filed: May 6, 1980

[30] Foreign Application Priority Data

May 14, 1979 [JP] Japan .................. 54-59481

[51] Int. Cl.$^3$ .................................. C07D 501/36
[52] U.S. Cl. ........................... 544/27; 424/246
[58] Field of Search .................. 544/21, 27, 26; 424/246

[56] References Cited

U.S. PATENT DOCUMENTS 4,146,710  3/1979  Naito et al. ............... 424/246
4,189,479  2/1980  Kakeya et al. ............. 544/27

Primary Examiner—Nicholas S. Rizzo
Attorney, Agent, or Firm—Craig and Antonelli

[57] ABSTRACT

Crystallized cephalosporin salts, particularly crystalline addition salt of pivaloyloxymethyl 7$\beta$-[2-(2-aminothiazol-4-yl)acetamido]-3-[[[1-(2-dimethylaminoethyl)-1H-tetrazol-5-yl]thio]methyl]ceph-3-em-4-carboxylate with hydrochloric acid, tartaric acid or citric acid, which is very stable and is readily adsorbable through intestinal tract, with little individual differences, when the salt is applied orally.

5 Claims, 4 Drawing Figures

CRYSTALLIZED CEPHALOSPORIN SALTS

The present invention relates to crystallized cephalosporin salts.

More particularly, the present invention relates to crystalline addition salts of pivaloyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate (hereinafter referred to simply as Compound-I) with hydrochloric acid, citric acid, or tartaric acid, and the method for producing the same.

Figure 1:
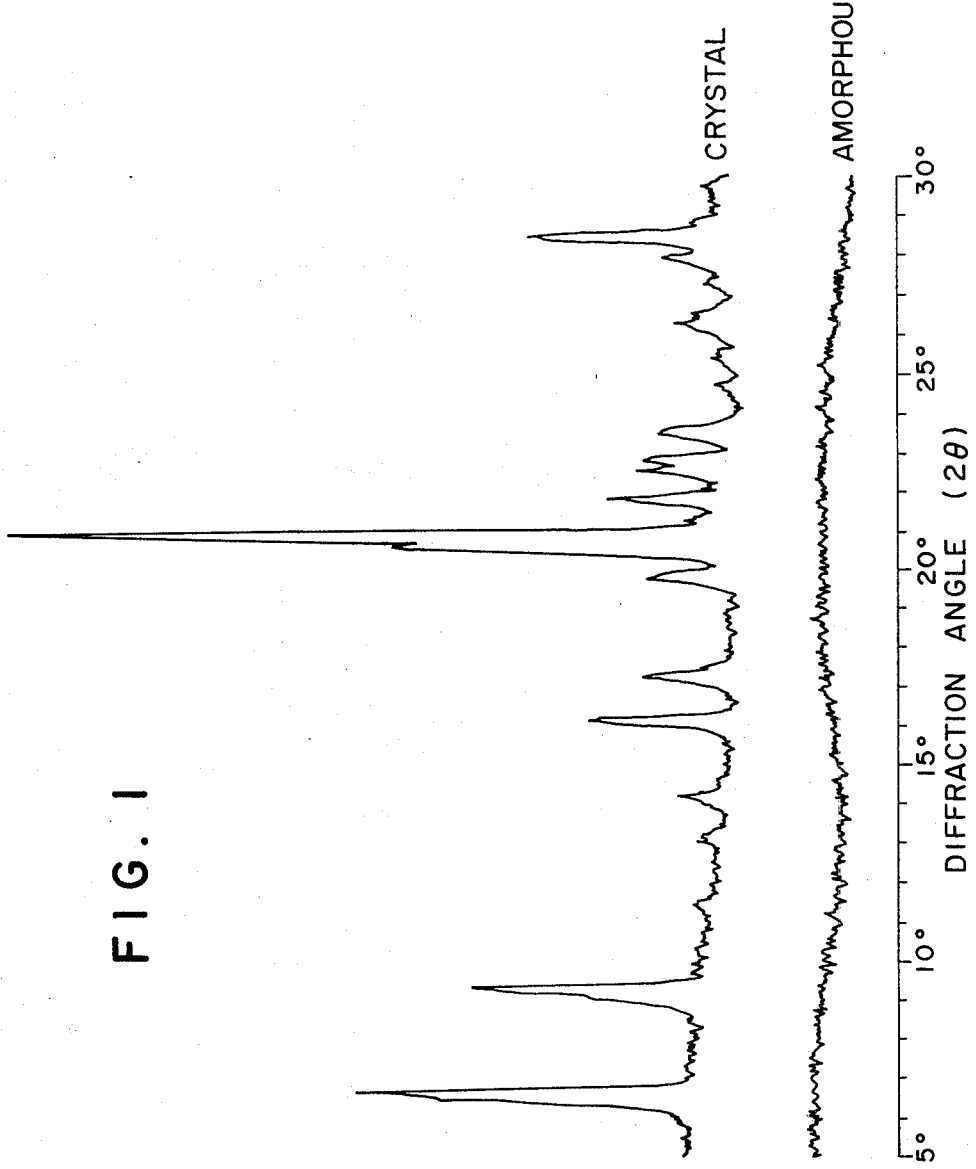
Figure 2:
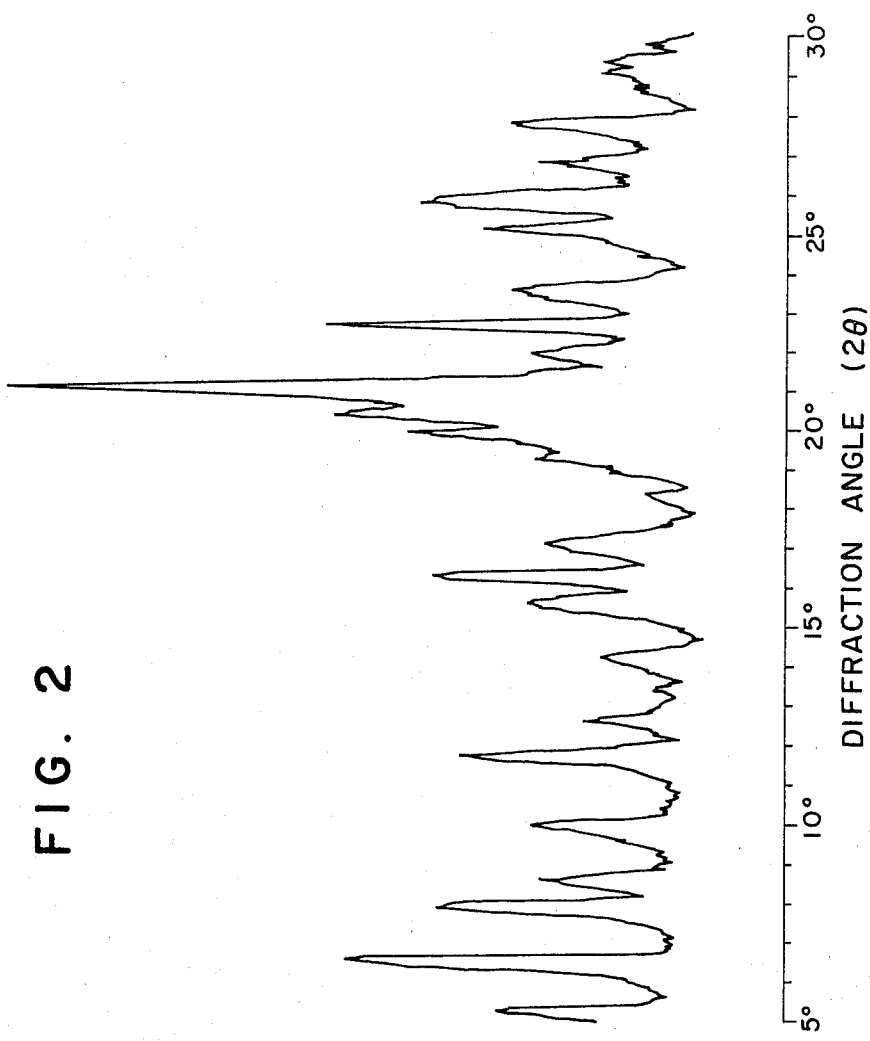
Figure 3:
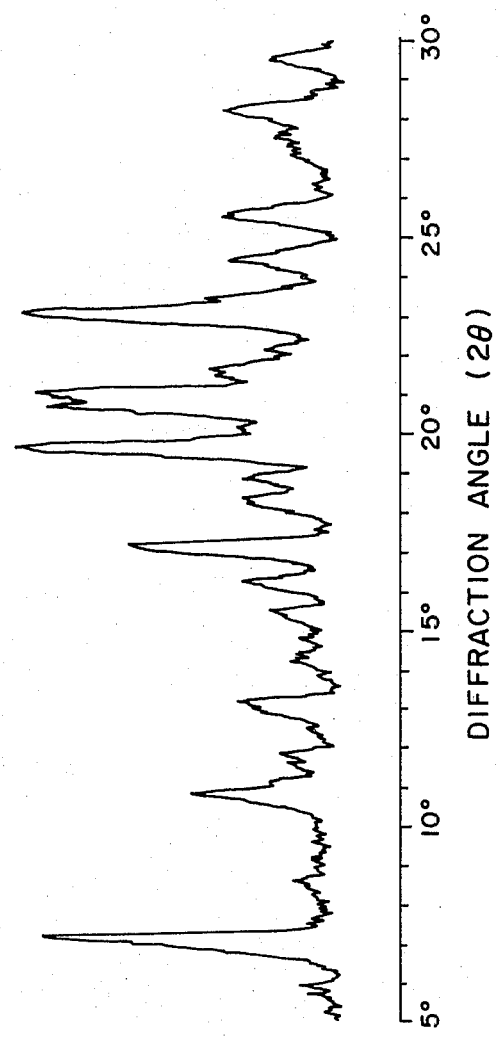

In the accompanying Drawings:

FIGS. 1, 2, and 3 represent the results of X-ray powder diffractions of the crystals of dihydrochloride, tartrate, and citrate, respectively, of pivaloyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

In FIG. 1, the results of X-ray powder diffraction of the amorphous dihydrochloride salt are also shown for the purpose of comparison.

Figure 4:
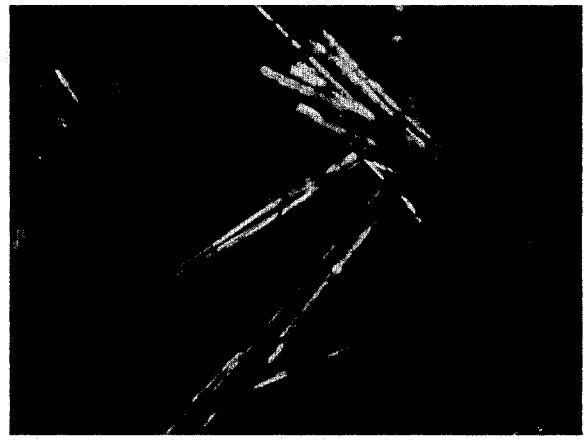

FIG. 4 represents the microscopic photogram of the dihydrochloride salt of the compound mentioned above. (X50, Union Optical Tokyo Metallomicrograph UM, Polaroid Positive/Negative Type 665).

Compound-I may be prepared, for instance, according to the method as described in OLS 2735732. Compound-I and its acid-addition salts are useful as orally administrable drugs for the treatment of bacterial infections because of their excellent antibiotic activity and absorbability through intestinal tract, as described in OLS. The present inventors have found that the addition salt of Compound-I with hydrochloric acid, citric acid, or tartaric acid, when it is formed in the crystalline state, comes to possess a remarkable stability, and to be absorbed readily through the intestinal tract, with little individual differences. According to the method of the present invention, crystalline addition salts of Compound-I with an acid can be produced through commercially convenient and safe procedure and also in a high yield. The crystalline acid addition salts produced according to the present method are excellent in the physical and chemical stabilities, and are suitable for the use as pharmaceuticals and for making the preparations.

The acid employed in the present invention is that which is pharmaceutically permissible, and is selected from hydrochloric acid, citric acid, and tartaric acid. The addition salt of Compound-I with acid, produced according to the present invention, means the salt from Compound-I and any of the acids as defined above.

The addition salt of Compound-I with hydrochloric acid, citric acid, or tartaric acid, is produced by reacting the Compound-I with any of the acids as defined above. In this method, the reaction is carried out in an aqueous medium (water or a mixture of water with the aqueous or hydrophilic solvent as described below). That is to say, Compound-I may be added to an aqueous solution of the acid for the reaction, or the acid may be added to an aqueous suspension containing Compound-I, for the reaction. Alternatively, Compound-I and the acid may be added to water at once, for the reaction.

The amount of Compound-I employed varies depending upon the solubility of the acid addition salt to be formed, but it may be approximately 1 to 30%, preferably 3 to 20% (weight/volume), based upon the aqueous medium (water). The amount of the acid employed may usually be about 2 to 10 molar amount per mole of Compound-I, though no difficulty is encountered by use of the excess amount. The reaction of Compound-I with the acid may usually be conducted at the room temperature, though it may be conducted at an elevated temperature, if necessary. Upon concentration or cooling of the reaction mixture, namely, an aqueous solution of the addition salt of Compound-I with the acid, obtained by the method as mentioned above crystals of the acid-addition salt are isolated. If there is any insoluble matter in the reaction mixture, it may desirably be removed in advance, for example, by filtration. The concentration of the reaction mixture is normally conducted under reduced pressure or in vacuo. For the cooling, lowering of the temperature of the reaction mixture from the room temperature down to about 0° to 5° C. is sufficient, in general. In some cases, the crystallization process as mentioned above may be carried out in the presence of an aqueous or hydrophilic solvent other than water, and/or salt, thereby to improve the properties of the isolated crystals and to increase the yield. Such aqueous or hydrophilic solvent may be, for example, an alcohol (such as methanol, ethanol, and isopropyl alcohol), a ketone (such as acetone and methyl ethyl ketone), dioxane, tetrahydrofuran, acetonitrile, or others, among which ethanol and acetone are conveniently used. The amount of the aqueous or hydrophilic solvent to be added is preferably up to about 40% (volume/volume) relative to the amount of the reaction mixture. The salt to be added may be, for example, sodium chloride sodium bromide, or calcium chloride, among which sodium chloride is conveniently used. The amount of the salt to be employed may usually be up to about 30% (weight/volume), preferably up to about 15% (weight/volume), relative to the total amount. Use of such aqueous solvent or the salt may not necessitate so low cooling temperature. Also, the aqueous solvent and the salt may be used concurrently.

The crystallization process may be effected repeatedly. Thus the once formed crystals may be separated, dissolved in water or an aqueous acid solution of said acid, and recrystallized in the same manner as described above.

The crystalline addition salt of Compound-I with an acid, thus-formed, can be separated and recovered from the reaction mixture by conventional procedures such as filtration, washing, and drying. The filtration and drying are desirably effected under a reduced pressure and a low temperature, within a short period of time.

The crystalline salts of Compound-I with hydrochloric acid, citric acid, or tartaric acid, thus-produced, may be of hydrate type. For example, the dihydrochloride salt is formed in anhydrous crystals, dihydrate ($2H_2O$) crystals or hexa- or heptahydrate ($6-7H_2O$) crystals, in which the dihydrate crystals are the most stable.

The crystalline acid-addition salt can be administered orally, for example, in the form of tablet, capsule, granules, or other preparation.

The present invention will be more concretely illustrated by the following examples and reference example, which, however, should not be construed to limit the scope of the invention.

EXAMPLE 1

Production of crystalline dihydrochloride:

(1) In 30 ml of dimethylacetamide is dissolved 2.9 g of potassium 7-β-[2-(2-aminothiazol-4-yl)acetamido]-3-[[[1-(2-dimethylaminoethyl)-1H-tetrazol-5-yl]thio]methyl]ceph-3-em-4-carboxylate, and the solution is cooled to a temperature of −15° C. To the solution, under stirring was added dropwise, over a period of 5 minutes, 4 ml of dimethylacetamide solution containing 1.3 g of iodomethyl pivalate, and the stirring is continued for additional 5 minutes. The reaction mixture is poured into 100 ml of ice-water, extracted with 100 ml of dichloromethane, and further extracted with 50 ml of the same solvent. The combined organic layer is washed with water and then with a saturated sodium chloride solution, and dried over anhydrous sodium sulfate. Evaporation of the solvent in vacuo leaves 2.0 g of colorless, powdered pivaloyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate. Two grams of Compound-I is dissolved in 7.5 ml of 0.5 N hydrochloric acid. After addition and dissolution of 15 g sodium chloride, the solution is cooled, thereby to isolate colorless needles of dihydrochloride of Compound-I.

(2) The crystals as obtained in the aforesaid process (1) is dissolved in 10 ml of 0.5 N hydrochloric acid, and the insoluble matter is filtered off. Addition of 0.5 ml of ethanol to the filtrate, followed by cooling, isolates colorless crystals, which are filtered, washed with a small amount of cold 0.5 N hydrochloric acid, and then dried in vacuo, to give 1.7 g of desired dihydrochloride of Compound-I in needles.

IR(KBr)cm$^{-1}$: 1775, 1730

NMR (100 MHz, in $D_2O$)δ: 1.24(s, $C(CH_3)_3$), 3.11(s, $N(CH_3)_2$), 3.6-4.1(m, $CH_2CO$ and $C_2$—H), 3.91(t, J=6 Hz, $NCH_2$), 4.24 and 4.42(ABq, J=14 Hz, $C_3$—H), 4.99(t, J=6 Hz, $NCH_2$), 5.20(d, J=4.5 Hz, $C_6$—H), 5.73(d, J=4.5 Hz, $C_7$—H), 5.80 and 5.97(ABq, J=6 Hz, —$OCH_2O$—), 6.74(s, thiazole 5—H)

Elemental analysis:

as $C_{24}H_{33}N_9O_6S_3 \cdot 2HCl \cdot 2H_2O$ (containing 0.79% NaCl)

Calcd.: C, 38.20; H, 5.21; N, 16.70%,

Found: C, 38.02; H, 5.07; N, 17.02%.

The product is confirmed to be crystalline from the results of X-ray powder diffraction and polarizing microscopic observation.

(3) In 700 ml of water is dissolved 53.6 g of wet crystals as obtained in the aforesaid process (1). The insoluble matter is filtered off. By addition of 100 g of sodium chloride to the filtrate under stirring, colorless crystals are isolated. After 2 hour standing, the crystals in needle form are collected by filtration and dried in vacuo, to give 16 g of the desired product.

IR(KBr)cm$^{-1}$: 1775, 1730

NMR (100 MHz, in $D_2O$)δ: 1.26(s, $C(CH_3)_3$), 3.16(s, $N(CH_3)_2$), 3.7-4.1(m, $CH_2CO$ and $C_2$—H), 3.93(t, J=6 Hz, $NCH_2$), 4.26 and 4.44(ABq, J=13.5 Hz), 5.00(t, J=6 Hz, $NCH_2$), 5.23(d, J=4.5 Hz, $C_6$—H), 5.74(d, J=4.5 Hz, $C_7$—H), 5.81 and 6.00(ABq, J=6 Hz, —$OCH_2O$—), 6.77(s, thiazole 5-H)

Elemental analysis:

as $C_{24}H_{33}N_9O_6S_3 \cdot 2HCl \cdot 2H_2O$

Calcd.: C, 38.50; H, 5.25; N, 16.84, Cl, 9.47%,

Found: C, 38.08; H, 5.14; N, 16.75; Cl, 9.70%.

The product is confirmed to be crystalline from the results of X-ray powder diffraction (FIG. 1) and polarizing microscopic observation (FIG. 4).

EXAMPLE 2

Production of crystalline monohydrochloride:

In 10 ml of water is dissolved 0.8 g of dihydrochloride of Compound-I. Under ice-cooling and stirring, to the solution is added dropwise 0.1 N—NaOH, to adjust the pH to 4.5. After further cooling and stirring continued, precipitates are formed from the solution, which are collected by filtration, washed with a small amount of cold water, and dried in vacuo, to give 0.45 g of the desired product.

IR(KBr)cm$^{-1}$: 1780, 1745

NMR(90 MHz, in $d_6$-DMSO)δ: 1.16(s, $C(CH_3)_3$), 2.75(s, $N(CH_3)_2$), 3.36(s, $CH_2CO$), 3.53(t, J=6 Hz, $NCH_2$), 3.67 and 3.88(ABq, J=16.5 Hz, $C_2$—H), 4.20 and 4.53(ABq, J=13.5 Hz, $C_3$-H), 4.72(t, J=6 Hz, $NCH_2$), 5.08(d, J=4.5 Hz, $C_6$—H), 5.6-5.8(m, $C_7$—H), 5.73 and 5.90(ABq, J=6 Hz, —$OCH_2O$—), 6.27(s, thiazole-5H), 6.9-7.5(b-s, $NH_2$), 8.88(d, J=9 Hz, CONH)

Elemental analysis:

as $C_{24}H_{33}N_9O_6S_3 \cdot HCl \cdot H_2O$

Calcd.: C, 41.58; H, 5.09; N, 18.19; S, 13.87; Cl, 5.11%,

Found: C, 40.95; H, 5.05; N, 18.08; S, 13.78; Cl, 5.48%.

The product is confirmed to be crystalline from the results of X-ray powder diffraction and polarizing microscopic observation.

EXAMPLE 3

Production of crystalline tartrate:

(1) In 6.5 ml of water is dissolved 0.31 g tartaric acid. To the solution, under stirring, is added 0.65 g of Compound-I. The insoluble matter is filtered off. To the filtrate is added 0.3 ml of ethanol and cooled, thereby to isolate colorless crystals, which are collected by filtration and dried in vacuo, to give 0.40 g of the desired product.

IR(KBr)cm$^{-1}$: 1780, 1740

NMR(90 MHz, in $D_2O$)δ: 1.30(s, $C(CH_3)_3$), 3.17(s, $N(CH_3)_2$), 3.7-4.15(m, $CH_2CO$ and $C_2$—H), 3.95(t, J=6 Hz, $NCH_2$), 4.25 and 4.50(ABq, J=13.5 Hz, $C_3$—H), 4.60(s, CH—CH), 5.06(t, J=6 Hz, $NCH_2$), 5.25(d, J=4.5 Hz, $C_6$—H), 5.75(d, J=4.5 Hz, $C_7$—H), 5.86 and 6.03(ABq, J=6 Hz, —$OCH_2O$—), 6.75(s, thiazole 5—H)

Elemental analysis:

as $C_{24}H_{33}N_9O_6S_3 \cdot 2C_4H_6O_6 \cdot H_2O$,

Calcd.: C, 40.12; H, 4.95; N, 13.16; S, 10.04%,

Found: C, 40.27; H, 5.19; N, 13.13; S, 10.92%.

The product is confirmed to be crystalline from the results of X-ray powder diffraction (FIG. 2) and polarizing microscopic observation.

(2) In 10 ml of water is dissolved 0.30 g of tartaric acid. In the solution, under stirring, is dissolved 0.65 g of Compound-I. The insoluble matter is filtered off, and 0.70 g of sodium chloride is dissolved in the filtrate. Upon cooling, colorless crystals are isolated, which are collected by filtration and dried in vacuo, to give 0.50 g of the desired product.

IR(KBr)cm$^{-1}$: 1780, 1740

NMR(90 MHz, in $D_2O$)δ: 1.31(s, $C(CH_3)_3$), 3.18(s, $N(CH_3)_2$), 3.8-4.1(m, $CH_2CO$ and $C_2$—H), 3.97(t, J=6 Hz, $NCH_2$), 4.26 and 4.51(ABq, J=13.5 Hz, $C_3$—H), 4.66(s, CH—CH), 5.07(t, J=6 Hz, $NCH_2$), 5.28(d, J=4.5 Hz, $C_6$—H), 5.79(d, J=4.5 Hz, $C_7$—H), 5.89 and 6.01(ABq, J=6 Hz, —$OCH_2O$—), 6.77(s, thiazole 5—H)

Elemental analysis:

as $C_{24}H_{33}N_9O_6S_3 \cdot 2C_4H_6O_6 \cdot 2H_2O$ (containing 1.31% NaCl), Calcd.: C, 34.22; H, 4.39; N, 11.23; S, 8.56%, Found: C, 33.65; H, 4.57; N, 12.45; S, 8.90%.

The product is confirmed to be crystalline from the results of X-ray powder diffraction and polarizing microscopic observation.

EXAMPLE 4

Production of crystalline citrate:

In 12 ml of water is dissolved 0.38 g of citric acid. In the solution, under stirring, is dissolved 0.65 g of Compound-I, whereupon crystals precipitate out immediately. After cooling, the crystals are collected by filtration washed with a small amount of cold water, and dried in vacuo, to give 0.46 g of crystalline desired product.

IR(KBr)cm$^{-1}$: 1785, 1750-1730

NMR(90 MHz, in $d_6$—DMSO)δ: 1.14(s, C(CH$_3$)$_3$), 2.29(s, N(CH$_3$)$_2$), 2.63 and 2.66(two-s, CH$_2$COOHx2), 2.83(t, J=6 Hz, NCH$_2$), 3.34(s, CH$_2$CO), 3.57 and 3.82(ABq, J=18.0 Hz, C$_2$—H), 3.98 and 4.32(ABq, J=13.5 Hz, C$_3$—H), 4.40(t, J=6 Hz, NCH$_2$), 5.04(d, J=4.5 Hz, C$_6$—H), 5.6-5.8(m, C$_7$—H), 5.73 and 5.89(ABq, J=6 Hz, —OCH$_2$O—), 6.4-7.2(b-s, NH$_2$, COOH and OH), 8.80(d, J=9 Hz, CONH)

Elemental analysis:

as $C_{24}H_{33}N_9O_6S_3 \cdot C_6H_8O_7 \cdot 1.5H_2O$,

Calcd.: C, 41.95; H, 5.16; N, 14.75; S, 11.20%,

Found: C, 41.87; H, 5.35; N, 14.71; S, 11.27%.

The product is confirmed to be crystalline from the results of X-ray powder diffraction (FIG. 3) and polarizing microscopic observation.

REFERENCE EXAMPLE

A mixture of 178 parts of dihydrochloride of pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate (125 mg/potency, calculated as the free carboxylic acid), 19 parts of crystalline cellulose (Avicel ®), and a small amount of magnesium stearate, as lubricant, is tabulated and then coated with hydroxypropylcellulose.

The tablets obtained have 125 mg potency/tablet. Each 2 tablets may be administered after meal.

We claim:

1. A crystalline dihydrate or anhydride of pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate dihydrochloride.

2. A method of producing a highly stable crystalline dihydrochloride of the ester pivaloyloxymethyl 7β-[2-(2-aminothiazol-4-yl)-acetamido]-3-[[[1-(2-dimethylaminoethyl)-1H-tetrazol-5-yl]thio]methyl]ceph-3-em-4-carboxylate, which comprises reacting the ester with hydrochloric acid and recovering the crystalline dihydrate or anhydride of the dihydrochloride from the resulting reaction mass.

3. A method as defined in the claim 2, wherein the crystalline compound is precipitated in the presence of acetone.

4. A method as defined in the claim 2, wherein the reaction mass resulted from the reaction is concentrated or cooled in the presence of ethanol.

5. A method as defined in the claim 2, wherein the reaction mass resulted from the reaction is concentrated or cooled in the presence of sodium chloride.

* * * * *